(12) United States Patent
Miller et al.

(10) Patent No.: US 6,542,846 B1
(45) Date of Patent: Apr. 1, 2003

(54) THERMAL MANAGEMENT SYSTEM FOR A PORTABLE ULTRASOUND IMAGING DEVICE

(75) Inventors: David G Miller, North Andover, MA (US); Joseph R Fallon, Boxford, MA (US); Dennis J. Buckley, Nashua, NH (US); Michael Hoar, Woburn, MA (US); Daniel Gerard Maier, Methuen, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 106 days.

(21) Appl. No.: 09/710,600

(22) Filed: Nov. 9, 2000

(51) Int. Cl.[7] ................................................ G01K 1/08
(52) U.S. Cl. ........................ 702/132; 361/1; 361/24; 361/27; 361/103; 361/106; 340/584
(58) Field of Search .............................. 702/132; 361/1, 361/27, 24, 103, 106; 323/267; 236/1; 340/584

(56) References Cited

U.S. PATENT DOCUMENTS

| | | |
|---|---|---|
| 5,590,658 A | 1/1997 | Chiang et al. |
| 5,603,323 A | 2/1997 | Pflugrath et al. |
| 5,636,631 A | 6/1997 | Waitz et al. |
| 5,690,114 A | 11/1997 | Chiang et al. |
| 5,715,823 A | 2/1998 | Wood et al. |
| 5,722,412 A | 3/1998 | Pflugrath et al. |
| 5,756,227 A | 5/1998 | Suzuki et al. |
| 5,773,956 A | 6/1998 | Wieczorek |
| 5,774,784 A | 6/1998 | Ohno |
| 5,795,664 A | 8/1998 | Kelly |
| 5,817,024 A | 10/1998 | Ogle et al. |
| 5,839,442 A | 11/1998 | Chiang et al. |
| 5,851,186 A | 12/1998 | Wood et al. |
| 5,879,303 A | 3/1999 | Averkiou et al. |
| 5,891,035 A | 4/1999 | Wood et al. |
| 5,893,363 A | 4/1999 | Little et al. |
| 5,897,498 A | 4/1999 | Canfield et al. |
| 5,938,607 A | 8/1999 | Jago et al. |
| 5,957,846 A | 9/1999 | Chiang et al. |

(List continued on next page.)

OTHER PUBLICATIONS

Terason 2000 information obtained from url: www.terason.com/terason2000.htm; 6 pages.

Sonosite 180 information obtained from url: www.sonosite.com/products_180_heart.html; 5 pages.

SonoHeart Applications Summary obtained from the SonoSite brochure; 2 pages.

Primary Examiner—John Barlow
Assistant Examiner—A Dougherty
(74) Attorney, Agent, or Firm—John Vodopia (57) ABSTRACT

A thermal management system for a portable battery powered electronic device, and particularly, a portable battery powered ultrasound device, which controls the temperature of the device such that the external surface temperature satisfies medical safety regulatory requirements, and such that the heat generated by the device does not reduce battery life, reduce component life, decrease reliability of the device, or cause device shutdown because of overheating. A thermal management system monitors the respective temperatures of various system components, and, based on the monitored temperatures, performs control to cool the ultrasound system, maintaining the external surface temperature below the safety regulated temperatures and ensuring reliability of system components. The thermal management system controls the system temperature and external surface temperature by various measures, including controlling operation of a cooling fan; modifying system parameters to change an operating mode of the ultrasound system; controlling clocking of the system circuitry by selectively enabling or disabling circuitry; and modifying a charging profile of the battery.

28 Claims, 5 Drawing Sheets

U.S. PATENT DOCUMENTS

| | | |
|---|---|---|
| 5,964,709 A | 10/1999 | Chiang et al. |
| 5,997,479 A | 12/1999 | Savord et al. |
| 6,007,490 A | 12/1999 | Pawluskiewicz |
| 6,013,032 A | 1/2000 | Savord |
| 6,102,863 A | 8/2000 | Pflugrath et al. |
| 6,106,468 A | 8/2000 | Dowdell |
| 6,106,472 A | 8/2000 | Chiang et al. |
| 6,113,547 A | 9/2000 | Catallo et al. |
| 6,117,084 A | 9/2000 | Green et al. |
| 6,117,085 A | 9/2000 | Picatti et al. |
| 6,134,667 A * | 10/2000 | Suzuki et al. ............... 318/471 |
| 6,135,961 A | 10/2000 | Pflugrath et al. |
| 6,255,622 B1 * | 7/2001 | May et al. .................. 219/201 |
| 6,286,109 B1 * | 9/2001 | Pirdy ......................... 320/106 |
| 6,349,385 B1 * | 2/2002 | Kaminski et al. ........... 361/688 |

* cited by examiner

THERMAL MANAGEMENT SYSTEM FOR A PORTABLE ULTRASOUND IMAGING DEVICE

TECHNICAL FIELD

The present invention generally relates to a thermal management system to control temperature of an electronic device and to provide a user with a visual indication of the temperature of the device. More particularly, the present invention is related to a small-sized, light-weight, portable, battery powered ultrasound imaging system having a thermal management system to provide temperature control and display of thermal conditions in the system.

BACKGROUND OF THE INVENTION

Portable electronic devices must be small in size, light weight and battery powered to provide the user of the device optimum mobility and ease of use. However, the requirements necessary to achieve portability result in severe constraints on space, weight and power dissipation in the device, causing an increase in the amount of heat generated by the components of the electronic device. The heat generated by the components contributes to an overall rise in the temperature of the device. For example, heat is generated by the various integrated circuit components of the device. Heat may also be generated by a rechargeable battery which powers the device, particularly when the device is in use while connected to an external power source and battery charging takes place.

The problem of heat generation in an electronic device is an extremely important concern with respect to portable battery powered diagnostic medical imaging devices wherein the device circuitry is complex and high power is required, and yet patient safety and device reliability must be ensured. In particular, while the high power and high circuit density required by the portable battery powered diagnostic medical imaging devices further exacerbate the problem of heat generation, the devices must satisfy certain medical safety requirements regulating the maximum external surface temperature of the device. Present medical safety requirements regulating temperature mandate that the maximum allowable external surface temperature of a medical device (i.e., the "skin" temperature) not exceed 50° C., thereby ensuring that contact with a patient will not result in patient discomfort or burning. More specifically, there exist several regulations and rules regarding the temperature of medical devices, such as IEC 60601. Those of ordinary skill in the art are well aware of the regulations. What is important is that if the heat generated by a device used in medical applications is not effectively dissipated, it is likely that the device will not satisfy the safety regulatory requirements.

Moreover, excessive heat generated by small portable electronic devices may have other adverse effects on the device, such as reduced battery life, reduced component life, decreased reliability of the device, or device shutdown.

Yet another problem associated with heat generation in current portable diagnostic medical device is that the user is not informed when overheating of the system is occurring, thereby depriving the operator of the opportunity to take appropriate action to alleviate the situation causing the overheating.

Thus, there is a need for a thermal management system in a portable battery powered electronic device, and particularly, in a portable battery powered diagnostic medical imaging device, which addresses the foregoing problems.

SUMMARY OF THE INVENTION

The present invention solves the foregoing and other problems by providing a thermal management system for a portable battery powered electronic device, and particularly, a portable battery powered ultrasound device, which controls the temperature of the device such that the external surface temperature satisfies medical safety regulatory requirements.

The present invention solves the foregoing and other problems by providing a portable electronic device, and particularly, a portable battery powered ultrasound device, which controls the temperature of the device such that the heat generated by the device does not reduce battery life, reduce component life, decrease reliability of the device, or cause device shutdown because of overheating.

The present invention solves the foregoing and other problems by providing a portable electronic device, and particularly, a portable battery powered ultrasound device, having a display for displaying an indication of system temperature to an operator in a simple, intuitive and easy-to-read manner to allow the operator to take action, or warn the operator of impending automatic actions, if the system temperature reaches unacceptable levels. The display is preferably an iconic display.

BRIEF DESCRIPTION OF THE DRAWINGS

These and other advantages of the present invention will become apparent and more readily appreciated from the following description of the preferred embodiments, taken in conjunction with the accompanying drawings, of which.

DETAILED DESCRIPTION OF THE PREFERRED EMBODIMENTS

Reference will now be made in detail to the preferred embodiments of the present invention, examples of which are illustrated in the accompanying drawings, wherein like reference numerals refer to like elements throughout.

Figure 1:
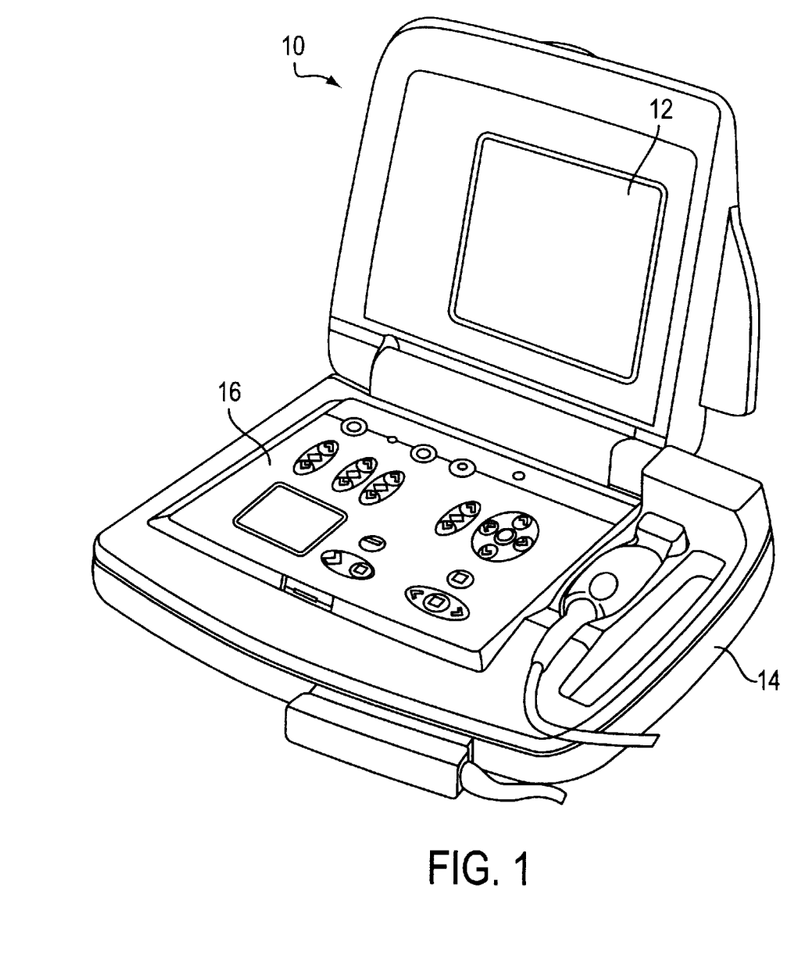
FIG. 1 is a perspective view of a portable battery powered ultrasound imaging system in accordance with the present invention.

FIG. 1 is a perspective view of a portable battery powered ultrasound imaging system 10 (hereinafter referred to as "the ultrasound system") for which thermal management is performed in accordance with preferred embodiments of the present invention. It will be appreciated by those of ordinary skill in the art that the present invention is not limited in its application to an ultrasound system, and is equally applicable to other types of electronic devices.

The ultrasound system 10 includes a display 12 on which an operator can view an ultrasound image, such as an image of an internal structure of the human body. The display 12 can also display other information, including iconic images indicating, for example, ultrasound imaging modes, system status, etc. The display 12 is preferably a liquid crystal display (LCD), but can be any display capable of displaying ultrasound image data and iconic images to an operator. A casing 14 forms an enclosure for the ultrasound system 10, housing the components of the ultrasound system 10. A lower section of the ultrasound system 10 includes operator input controls 16 for operating the ultrasound system 10, including, for example, controls to turn the system on and off, or to select various known operating modes, such as large sector, small sector, color flow, or other known modalities.

Various internal components of the ultrasound system 10, which are not shown in FIG. 1, are housed within the casing 14, including a printed circuit (PC) board on which ultrasound system circuitry is mounted, a rechargeable battery to power the ultrasound system 10, and at least one cooling fan to cool the ultrasound system 10. The ultrasound system 10 can operate using power supplied from the rechargeable battery, or, alternatively, the ultrasound system 10 can operate using power from an external power source that charges the rechargeable battery while the ultrasound system 10 is operating. The ultrasound system circuitry, rechargeable battery and cooling fan(s) will be described in more detail hereinbelow.

The ultrasound system 10 is small in size and light weight, allowing a high degree of mobility when used in medical diagnostic applications. In accordance with preferred embodiments of the present invention, the entire portable ultrasound system 10 weighs less than fifteen (15) pounds. Such weight reduction is possible through the studious selection of critical components.

During operation of the ultrasound system 10, power supplied to the ultrasound system circuitry causes the circuitry to generate heat as a result of power dissipation. The rechargeable battery also generates heat, particularly as a result of power dissipation during a charging operation.

In accordance with the present invention, the heat generated by the ultrasound system circuitry and rechargeable battery is controlled, thereby preventing the temperature of the system circuitry and rechargeable battery from reaching levels affecting reliability of operation. Furthermore, the heat generated by the ultrasound system is controlled to prevent the casing 14 external surface temperature from increasing beyond the temperature mandated by medical safety regulations.

As will be described in detail below, in accordance with the present invention, the temperature of the ultrasound system 10 is controlled by a thermal management system. The thermal management system monitors the respective temperatures of various system components, and, based on the monitored temperatures, performs control to cool the ultrasound system 10 and to maintain the external casing temperature below the safety regulated temperatures. Moreover, the thermal management system includes a display 12 to provide a visual indication of the system temperature and/or whether the system is in an overheated state, allowing an operator of the ultrasound system 10 to easily ascertain whether the ultrasound system 10 is overheating and whether the casing 14 temperature is approaching or has reached unacceptable levels.

The thermal management system in accordance with the present invention will now be described below, with reference to FIGS. 2 through 5.

Figure 2:
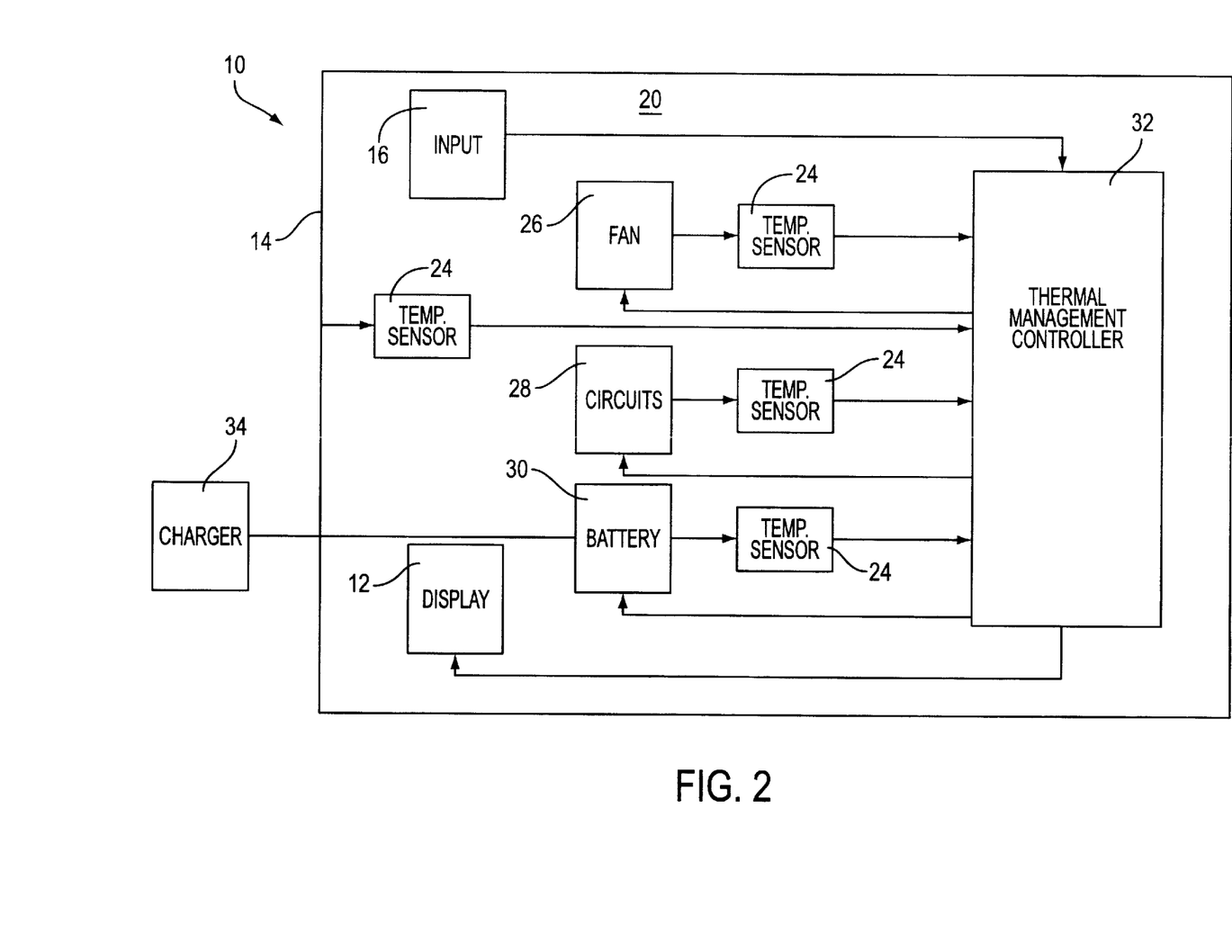
FIG. 2 is a simplified block diagram of an ultrasound system having a thermal management system in accordance with the present invention.

FIG. 2 is a block diagram of an ultrasound system 10 having a thermal management system 20 in accordance with the present invention.

As shown in FIG. 2, the thermal management system 20 includes a plurality of temperature sensors 24 to monitor the temperature of various components of the ultrasound system 10. The temperature sensors 24 are preferably thermistors, but could be integrated circuits, which are mounted in, on or near the various components, to monitor the respective temperatures of the components. In accordance with preferred embodiments of the invention, the temperature sensors 24 sense the respective temperatures of an area near a cooling fan 26, of selected integrated circuits (ICs) 28 in the ultrasound system 10, of a rechargeable battery 30, and of the external surface of the casing 14. The temperatures of the cooling fan 26, integrated circuits 28, rechargeable battery 30, and the external surface of the casing 14 are monitored by the temperature sensors 24 continuously throughout operation of the ultrasound system 10.

The temperature sensors 24 that monitor temperatures of the integrated circuits 28 and the temperature sensor 24 near the fan 26 are preferably thermistors located on the back side of the PC board which mounts the integrated circuits 28. Placing the temperature sensors 24 on top of or at other positions with respect to the integrated circuits 28 requires additional leads to connect the temperature sensors 24. As will be described in more detail below with reference to FIG. 4, the integrated circuits 28 monitored by the temperature sensors 24 are preferably the larger integrated circuits 28 having the greatest power dissipation, and corresponding heat generation.

The battery 30 is preferably a rechargeable smart battery, such as that manufactured by MOLTECH ENERGY SYSTEMS, which conforms to Smart Battery System (SBS) specifications. The smart battery 30 includes a built-in temperature sensor 24, preferably a thermistor, to sense the battery 30 temperature. An external charger 34 charges the battery 30. The battery 30 may be charged during operation of the ultrasound system 10.

A thermal management controller 32 periodically polls the temperature sensors 24 during operation of the ultrasound system 10 according to a software polling routine stored in the thermal management controller 32, thereby reading the plurality of temperatures sensed by the temperature sensors 24. The temperature values sensed by the temperature sensors 24 are analog values that are converted to digital values by an A/D converter (not shown), and read by the thermal management controller 32. As will be described in detail below, the thermal management controller 32 uses the sensed temperatures to decide which of a variety of different types of control should be performed to reduce the ultrasound system 10 temperature, and particularly, to reduce the temperature of the external surface of the casing 14.

Although the thermal management system 20 described with reference to FIG. 2 monitors the temperatures of each of the cooling fan 26, ICs 28, battery 30 and external casing 14 temperature, it is, of course, possible to monitor only selected portions of the ultrasound system 10. For example, it is possible to monitor only the temperature of the external casing 14. Further, it is possible to monitor only the temperatures of the ICs 28. Alternatively, it is possible to monitor only the temperatures of the ICs 28 and the battery 30. When only the ICs 28, or only the ICs 28 and battery 30 are monitored, the external casing 14 temperature is determined using a software model of the casing 14 stored in the thermal management controller 32. The software model of the casing 14 determines how much the casing 14 external surface temperature will increase based on a correlation between the amount of internal power dissipation, the internal temperature of the casing 14, and the type of casing 14 material. Such modeling is known and is usually performed with the aid of a software package such as FLOWTHERM.

Further, it is possible to monitor only the temperature of the external surface of the casing 14. When monitoring the temperature of the external surface of the casing 14, the temperature sensor 24 is preferably mounted on the hottest portion of the casing 14, which as noted above can be determined via modeling, but also can be determined through testing of prototype units.

The various types of control performed by the thermal management controller 32 will now be described in detail below. The thermal management controller 32 preferably includes a computer readable storage medium encoded with processing instructions to implement operations to control the temperature of the ultrasound system 10 components and to control the external surface temperature of the casing 14.

The two primary goals of the thermal management system 10 are to control the external surface temperature of the casing 14 to ensure that the casing 14 temperature does not increase beyond a temperature mandated by safety regulations, and to control temperature such that the junction temperatures of the ultrasound system 10 integrated circuits 28 do not exceed the manufacturer's specification. If the temperature of the integrated circuit 28 exceeds the manufacturer's specification, the electrical characteristics of the circuit 28 are no longer guaranteed and erratic operation may result.

The different types of control performed by the thermal management controller 32 to control system temperature include controlling operation of the cooling fan 26; modifying system parameters to change an operating mode of the ultrasound system 10; controlling clocking of the system circuitry; selectively enabling or disabling selected ICs 28; modifying a charging profile of the battery 30; controlling the display 12 to display an icon informing the operator of the system temperature or whether the system is in an overheated state, thereby allowing the operator to take action to reduce temperature; automatically powering off the device if the temperature level reaches an unacceptably high level; or any combination of the these types of control.

The simplest type of control that can be performed by the thermal management controller 32 to control temperature is controlling the cooling fan 28 to turn the cooling fan 28 on and off. Alternatively, rather than simple ON/OFF control of the cooling fan 28, the speed of the fan 28 can be modulated to vary the speed of the fan 28.

Another type of control that is performed by the thermal management controller 32 to control temperature involves controlling system parameters and clocking to control power dissipation. More specifically, because temperature rise in the ultrasound system 10 is related to the amount of power dissipation in the system, the thermal management system 20 can control the temperature of the ultrasound system 10 by controlling power dissipation in the system components. The power dissipation can be controlled in a variety of ways, which are related to the dynamic power consumption in the system. More particularly, the power consumption by the electrical circuits can generally be classified into a static component of power consumption and a dynamic component of power consumption. The static component of power consumption is a relatively constant amount of power the circuits 28 will consume during operation. The dynamic component of power consumption varies as a function of the clock speed and the type of digital activities occurring within the integrated circuit chip. For example, in most CMOS devices, the static power consumption is very small, and the dynamic power consumption is the vast majority of the power budget.

Thus, the thermal management controller 32 can control the dynamic power consumption of the integrated circuits 28 by modifying system parameters and/or by selectively enabling and clocking the various circuits 28, thereby reducing temperature in the ultrasound system 10.

In accordance with the present invention, the thermal management controller 32 modifies system parameters, such as those parameters controlling sector size, scan line and/or frame rate timing, transmit voltage, number of transmit pulses, and number of active system channels, to control temperature. By way of example, the imaging mode can be changed between a small sector and/or low frame rate mode consuming low power, a large sector and/or high frame rate mode consuming medium power and a color flow mode consuming high power.

However, as the system parameters are changed, the ultrasound image changes, and image quality is impacted. Therefore, it is preferable that thermal management controller 32 inform the operator that the imaging mode is changing by displaying an indication on the display 12. Alternatively, the operator inputs 16 may include a key input for the operator to enter a power-miser mode to conserve power when the ultrasound system 10 gets too hot.

The thermal management controller 32 can also turn off clocks in certain circuits 28 to reduce power dissipation and to thereby reduce temperature. More particularly, the ultrasound sector image is considered a series of scan lines. Each scan line includes several operational states, specifically, a download state, a transmit state, a receive state and an idle state. The various states of operation occur separately. For example, during the download state, transmitting and receiving do not occur. Therefore, during the download state, clocks associated with transmitting and receiving can be disabled. Similarly, during the transmit state, the receiver clocks can be disabled. During the receive state, the transmitter clocks can be disabled. If the various circuitry 28 is not clocked at times when the clock is not needed, the dynamic power consumption drops off significantly.

Those of ordinary skill in the relevant arts will also appreciate that the above-described control measures to reduce the temperature of the ultrasound system 10 by controlling power dissipation of the integrated circuits 28 can also be used to save power in the ultrasound system 10, even when not used in the context of controlling temperature in the ultrasound system 10.

The thermal management controller 32 can also control the system temperature by modifying the charging profile of the battery 30. The battery 30 contributes a large amount of heat to the system, especially during charging, because the battery 30 acts as a large resistor at the end of charging, and dissipates power. Near the end of charging, the battery 30 continues to accept current, but dissipates the current as heat. Therefore, by monitoring the temperature of the battery 30, the charging rate of the battery 30 can be reduced in response to detecting an increase in the temperature of the battery to control heat generation.

As discussed above, the battery 30 is a known type of smart battery having a built-in temperature sensor and is connected to the thermal management controller 32 via a known smart battery interface. The smart battery 30 also includes a built-in charging algorithm. The smart battery 30 can also inform the thermal management controller 32 of the type of chemistry of the battery 30. The battery 30 is preferably a Lithium-ion battery. However, the battery 30 may also be a nickel-metal-hydride battery or other appropriate type of battery.

When the battery 30 heats up, the outside temperature of the casing 14 can exceed the safety regulated temperature. The thermal management controller 32 polls the smart battery interface and determines the battery 30 temperature. The charging algorithm is controlled in response to the detected battery 30 temperature such that when the limit for safe operating temperature is approached, the charging rate is reduced such that the battery remains completely charged, and yet the battery temperature does not increase beyond acceptable levels.

Figure 3:
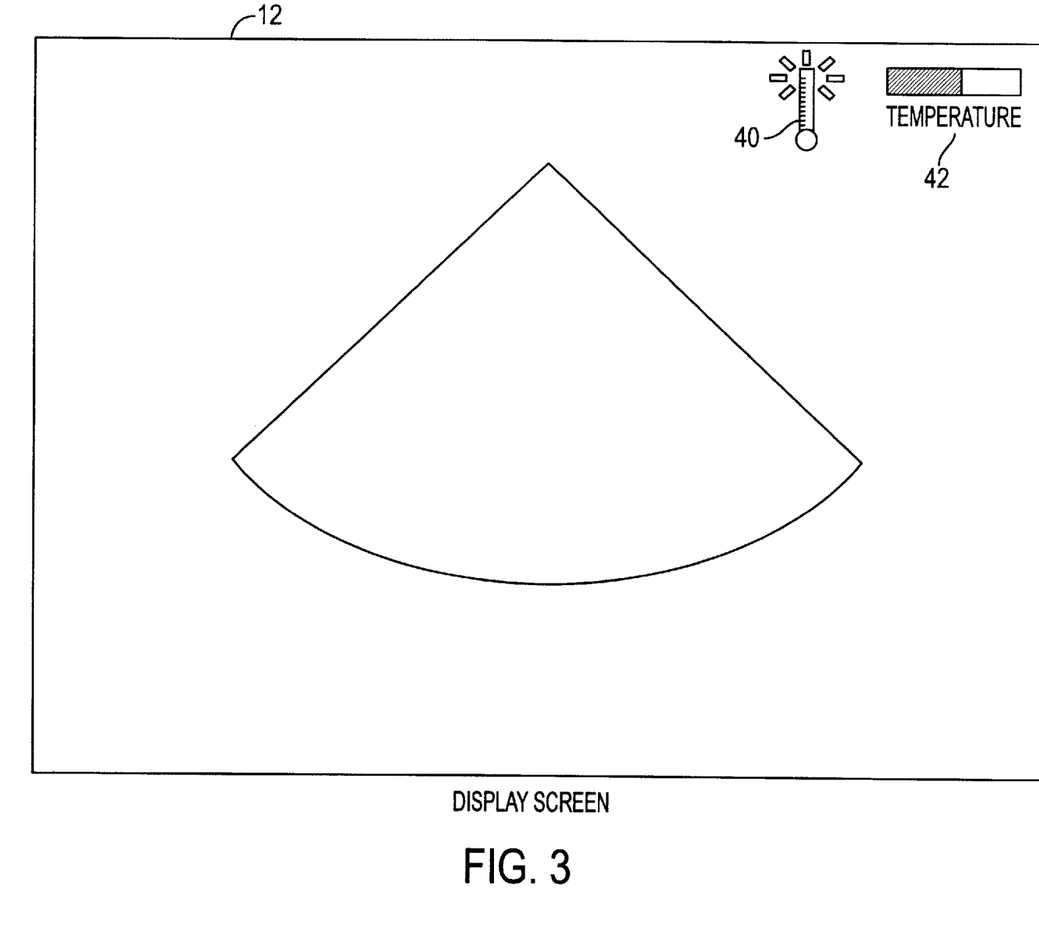
FIG. 3 is a diagram of an iconic display screen in accordance with the present invention.

The thermal management controller 32 can also control the ultrasound system 10 to provide a display indicative of the system temperature and/or an overheated status of the system. As shown in FIG. 3, which is a diagram of the ultrasound system display 12, an icon 40 can be displayed in response to the detected temperatures, indicating that the external surface temperature of the casing 14 has reached a critical temperature. The icon 40 informs the operator that the critical temperature has been reached, and that it is necessary for the operator to take action to alleviate heat. For example, if the icon 40 is displayed, the operator can manually change imaging modes or turn the system off to reduce heat.

Alternatively, the thermal management system 32 can display an icon 42 that provides an indication that the critical temperature is approaching, allowing an operator to see how quickly the ultrasound system 10 is heating up.

The thermal management controller 32 can also automatically power off the ultrasound system 10 in response to the detected temperature reaching an unacceptable level. However, automatic powering off of the ultrasound system 10 is not preferred because it is disruptive to the operator.

Figure 4:
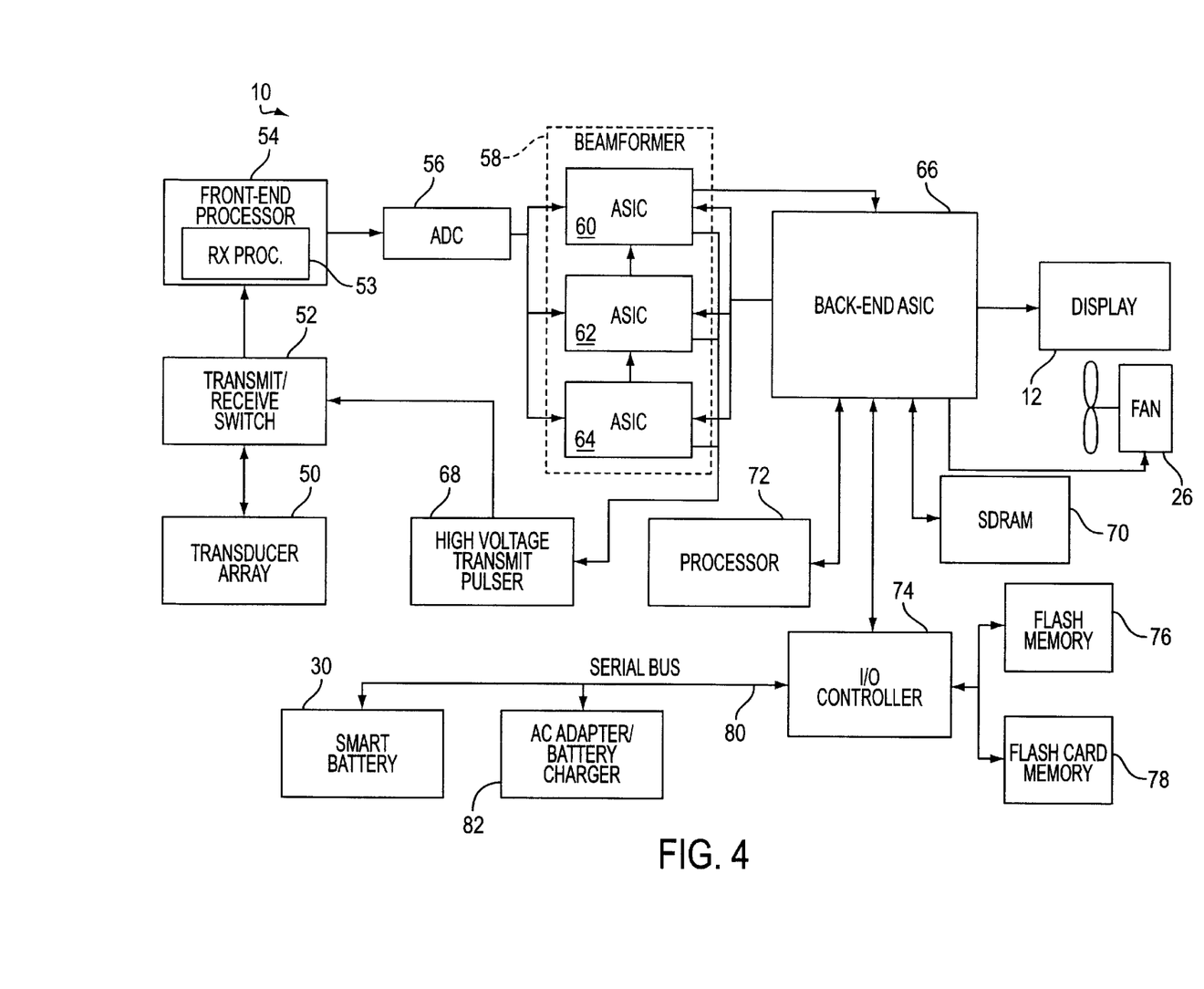
FIG. 4 is a detailed block diagram of an ultrasound system including the thermal management system in accordance with the present invention.

FIG. 4 is a detailed block diagram of the ultrasound system 10 having a thermal management system 20 in accordance with preferred embodiments of the present invention. It will be appreciated by those of ordinary skill in the relevant arts that the present invention is not limited in its application to the type of ultrasound system 10 shown in FIG. 4, and is equally applicable to other types of ultrasound devices or to any electronic device for which temperature control is needed. Although not all of the components shown in FIG. 4 are directly related to the present invention, all components shown in FIG. 4 will be described for completeness.

The ultrasound system 10 includes a sector phased array 50 having transducer elements, which transmits ultrasonic energy to a target and receives reflected ultrasonic energy from the target. The number of transducer elements corresponds to the number of signal channels. A transmit/receive switch 52 isolates transmit pulses used to interrogate a particular scan direction energy from the received ultrasound energy and delivers the received signals (one for each transducer element) via a connection to a front-end processor 54. Although illustrated as a single block in FIG. 3, the front end processor 54 may be implemented as one or more application specific integrated circuits (ASICs).

The front-end processor 54 includes a receive processor 53, which receives each of the received ultrasonic energy signals from each transducer element within sector phased transducer array 50 and performs amplification and filtering of the received signals.

The output of front-end processor 54 is supplied to analog-to-digital converter (ADC) 56. ADC 56 digitizes the samples for each channel and supplies a digital bit stream for each channel to a beamformer 58. The appropriate channels from the ADC 56 are supplied to ASICs 60, 62 and 64 within the beamformer 58. Each of the ASICs 60, 62 and 64 also provides a low voltage transmit timing signal to drive a high voltage transmit pulser 68.

The output of the beamformer 58 is taken from ASIC 60 and supplied as a beamformed signal to a back-end processor 66. The back-end processor 66 is typically implemented in one or more ASICs and is therefore typically referred to as a back-end ASIC.

Back-end ASIC 66 performs many processing functions. Back-end ASIC 66 also provides to beamformer 58 the coefficient data that allows each of the ASICs 60, 62 and 64 within beamformer 58 to perform the beamforming function and to perform the transmit timing necessary to generate low voltage transmit signal timing pulses.

The low voltage transmit timing signals are taken from beamformer 58 and supplied to the high voltage transmit pulser 68. Transmit pulser 68 then supplies the transmit pulses to transmit/receive switch 52. Transmit/receive switch 52 routes these transmit pulses to each corresponding transducer element within sector phased array 50.

Back-end ASIC 66 processes the signal supplied from the beamformer 58 and provides an ultrasonic image where it is displayed on the display 12. Back-end ASIC 66 also communicates with a static/dynamic random access memory element 70. The memory element 70 is used for intermediate data storage, storing processing code, tables, and all other executable software used by back-end ASIC 66.

In accordance with the present invention, the memory element 70 stores processing instructions for polling the temperature sensors 24, modeling the external surface temperature of the casing 14, and for controlling components of the ultrasound system 10 (e.g., fan 26, battery 30, system parameters, clocking, display 12, etc.) to control temperature.

Back-end ASIC 66 also communicates with a processor 72. Processor 72 is preferably a 7xx series processor sold under the trademark POWERPC, which is a registered trademark of Motorola Corporation. However, processor 72 can be any processor suitable for processing the received ultrasonic signals. The processor 72 uses standard personal computer (PC) tools and compilers. The software is upgradable, and designed in flexibility of the hardware, such as clocking agility including modifiable frequency output and the use of a connectorized transducer, multiple transducers with modifiable operating frequencies can be used. All such software is contained in the memory element 70 and executed in the processor 72.

The back-end ASIC 66 also communicates with an input/output (I/O) controller 74. I/O controller 74 controls the input and output tasks of the ultrasound system 10. For example, I/O controller 74 includes a keyboard input for communicating information into the ultrasound system 10, and includes serial and parallel ports for the connection of peripheral devices (not shown). I/O controller 74 also communicates with a flash memory element 76 and a flash card memory 78. Flash memory element 76 is a non-volatile memory that is used to store the current executable software files (sometimes referred to as the "run-time code") that enable the ultrasound system 100 to function. Flash card memory 78 is a removable storage media and is used to conveniently update the operating system executed by the ultrasound system 10. Furthermore, the ultrasound system 10 uses modifiable processing algorithms to perform different imaging applications, scanning formats, operating modes and aperture modes. These modifiable processing algorithms are implemented in software, which is stored in memory element 70 and executed by processor 72. The modifiable processing algorithms are in modular format and can be updated through the use of flash card memory 78 through the I/O controller 74. In this manner, software upgrades can be supplied to the ultrasound system 10 and stored in flash memory clement 76 by using simple transportable flash card memory element 78.

The I/O controller 74 also communicates via serial bus with smart battery 30 and alternating current (AC) adapter/battery charger 82. AC adapter/battery charger 82 provides power to the ultrasound system 10 in the absence of a battery, and, if present, charges the smart battery 30. In addition, the ultrasound system 10 includes a separate stand-alone battery charger (not shown) for charging the smart battery 30 when the battery is not installed in the system.

In accordance with preferred embodiments of the present invention, the temperature sensors 24 (not specifically shown in FIG. 3) are located to sense the temperatures of the front-end processor 54, the back-end ASIC 66, the processor 72, and near the fan 26. The respective circuits 54, 66, 72 that are monitored are selected based on the amount of power dissipation of the circuits.

An operational process performed by the thermal management controller 32 to control temperature in the ultrasound system 10 will now be described below with reference to FIG. 5.

In accordance with preferred embodiments of the present invention, the plurality of system temperatures sensed by temperature sensors 24 are monitored continuously throughout operation of the ultrasound system 10. The thermal management controller 32 compares the respective sensed temperatures with a plurality of selected critical temperature levels, for example, temperature levels A, B, C, D, etc., where temperature level A<temperature level B<temperature level C<temperature level D, etc. The critical temperature levels A, B, C, D, etc., are temperature levels used to determine the types of control performed to reduce the ultrasound system 10 temperature based on the result of the comparison between the temperatures detected by the temperature sensors 24 and the critical temperature levels A, B, C, D, etc. The critical temperatures are selected with reference to the applicable rules and regulations of the jurisdiction in question, such as IEC 60601.

The thermal management controller 32 preferably stores tables including a hierarchical list of the types of action taken to control temperature corresponding to the temperature levels A, B, C, D, etc. The hierarchical list of the type of action to control temperature may include a single action taken corresponding to a detected temperature level or a plurality of actions taken at the same time to control temperature.

In accordance with preferred embodiments of the present invention, the highest detected temperature value of the plurality of temperatures sensed by the temperature sensors 24 is used to decide the temperature control action taken. More specifically, if any one of the sensed temperature values exceeds a critical temperature level A, B, C, D, then corresponding temperature control action is taken, regardless of the other sensed temperatures. However, rather than using the highest temperature value to decide the control action a calculated value, such as a modeled value, an average or a weighted average of the detected temperatures can be compared to the critical temperature levels A, B, C, D to decide what action is taken. For example, if it is determined that a certain component contributes a greater proportion of heat to the system, that component can be given a greater weight.

Figure 5:
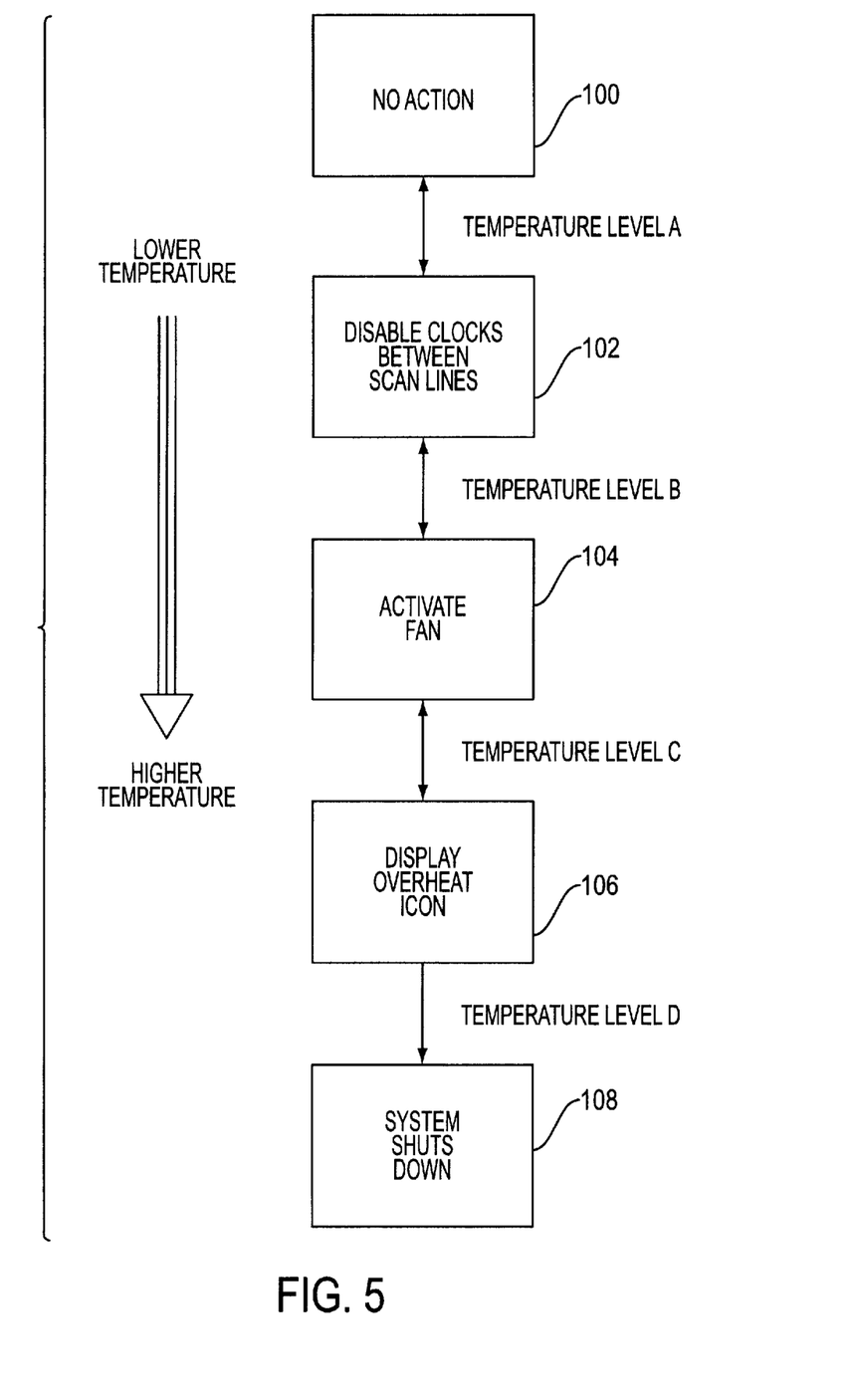
FIG. 5 is a flow chart of an operational process for controlling temperature in an ultrasound system in accordance with the present invention.

Referring now to FIG. 5, which is a flow chart illustrating an example of an operational process performed to control the ultrasound system 10 temperature in accordance with the present invention, initially, in operation 100, no action is taken because none of the sensed temperatures exceed a minimum critical temperature level A. However, if the highest sensed temperature value falls between temperature levels A and B, then the thermal management controller 32 takes action in operation 102 to control the clocking to disable clocks between scan lines to reduce temperature. If the highest sensed temperature value falls between temperature levels B and C, then, in operation 104, the thermal management controller 32 controls the cooling fan 26 to cool the ultrasound system 10. The action of disabling clocks in operation 102 is performed along with the control of the cooling fan 26 in operation 104. Next, if the highest sensed temperature value is between temperature levels C and D, an overheat icon 40 is displayed in operation 106, indicating that the ultrasound system 10 is approaching an unacceptable temperature level with respect to either the external temperature of the casing 14, the internal temperature, or both. At this time, the operator should take action to alleviate the excess heat. Finally, in operation 108, if the highest sensed temperature value is greater than temperature level D, the thermal management controller 32 automatically shuts off the ultrasound system 10.

Of course, it will be recognized that the present invention is not limited to the control operations performed in the example of FIG. 5, and that the hierarchy of the temperature control action and corresponding critical temperature levels can be suitably selected depending on the type of system being cooled and the extent of cooling required. Furthermore, the various temperature control actions can be performed individually or in any combination to control the ultrasound system 10 temperature.

Although preferred embodiments of the present invention have been shown and described, it will be appreciated by those skilled in the art that changes may be made in these embodiments without departing from the principle and spirit of the invention, the scope of which is defined in the appended claims and their equivalents.

What is claimed is:

1. A thermal management system for an electronic device, comprising:

a plurality of temperature sensors sensing respective temperatures of different portions of the electronic device;

a thermal control device controlling temperature of the electronic device based on the plurality of sensed temperatures; and a casing housing the electronic device, wherein the thermal control device controls heat generation in the electronic device to maintain a casing temperature below a predetermined temperature, wherein the thermal control device further comprises an icon configured to display an indication that a temperature of the casing is approaching an overheated state, the thermal control device further configured to perform a thermal control device hierarchy of control that first disables clocks, then controls a cooling fan, and finally displays an indication that a temperature of the electronic device exceeds a predetermined temperature.

2. The thermal management system as recited in claim 1, wherein the plurality of temperature sensors are thermistors.

3. The thermal management system as recited in claim 1, wherein the electronic device is a portable battery powered ultrasound imaging system.

4. The thermal management system as recited in claim 3, wherein the portable battery powered ultrasound imaging system weighs less than fifteen pounds.

5. The thermal management system as recited in claim 1, wherein the electronic device comprises circuitry and a rechargeable battery, wherein the casing further housing the circuitry and rechargeable battery, and wherein the temperature sensors sense respective temperatures of the circuitry, rechargeable battery and casing.

6. The thermal management system as recited in claim 1, wherein the thermal control device further comprises a cooling fan to control temperature of the electronic device.

7. The thermal management system as recited in claim 1, wherein the thermal control device further comprises a clocking controller selectively disabling clocks of components of the electronic device to control temperature.

8. The thermal management system as recited in claim 1, wherein the electronic device further comprises a rechargeable battery, and the thermal control device further comprises a battery charging controller controlling charging of the rechargeable battery to control temperature.

9. The thermal management system as recited in claim 1, wherein the thermal control device further comprises an operating mode changing device changing an operating mode of the electronic device to control temperature.

10. The thermal management system as recited in claim 1, wherein the thermal control device further comprises an automatic shut-off device automatically shutting off the electronic device to control temperature.

11. The thermal management system as recited in claim 1, wherein the thermal control device further controls heat generation of electronic device circuitry to control temperature.

12. The thermal management system as recited in claim 1, wherein the thermal control device further comprises a display displaying a temperature of the electronic device.

13. The thermal management system as recited in claim 1, wherein the thermal control device further comprises a cooling fan, a clocking controller selectively disabling clocks of components of the electronic device, and a display displaying the indication that the temperature of the electronic device exceeds the predetermined temperature, and wherein the thermal control device performs hierarchical control of the cooling fan, the clocking controller and the display based on temperatures detected by the temperature sensors to control the temperature of the electronic device.

14. The thermal management system as recited in claim 13, wherein the thermal control device compares a highest detected temperature with a plurality of predetermined temperature levels to determine the hierarchical control action.

15. The thermal management system as recited in claim 1, wherein the electronic device further includes a rechargeable battery, and the thermal control device further comprises a cooling fan, a clocking controller selectively disabling clocks of components of the electronic device, an operating mode changing device changing an operating mode of the electronic device, a battery charging controller controlling charging of the rechargeable battery, a display displaying the indication that the temperature of the electronic device exceeds the predetermined temperature, and an automatic shut-off device powering off the electronic device, wherein the thermal control device performs hierarchical control of the cooling fan, the clocking controller, the operating mode changing device, the battery charging controller, the display and the automatic shut-off device based on temperatures detected by the temperature sensors to control the temperature of the electronic device.

16. A thermal management system for an electronic device, comprising:

a plurality of temperature sensors sensing respective temperatures of different portions of the electronic device;

a thermal control device controlling temperature of the electronic device based on the plurality of sensed temperatures; and a casing housing the electronic device, wherein the thermal control device controls heat generation in the electronic device to maintain a casing temperature below a predetermined temperature, wherein the thermal control device further comprises a display displaying an indication that a temperature of the casing is approaching an overheated state, wherein the display is an icon, and wherein a thermal control device hierarchy of control first disables clocks, then controls a cooling fan, and finally displays an indication that a temperature of the electronic device exceeds a predetermined temperature.

17. A portable, battery powered ultrasound imaging system, comprising:

a temperature sensing device sensing a temperature of the ultrasound system;

a thermal management system including a plurality of different temperature controls controlling temperature of the ultrasound system based on the sensed temperature; and a casing housing the ultrasound system, wherein the thermal management system controls heat generation in the ultrasound system to maintain a casing temperature below a predetermined temperature, wherein the thermal management system further comprises an icon configured to display an indication that a temperature of the casing is approaching an overheated state, wherein the thermal management system is further configured to perform a thermal management system hierarchy of control that first disables clocks, then controls a cooling fan, and finally displays an indication that a temperature of the ultrasound system exceeds a predetermined temperature.

18. The ultrasound imaging system as recited in claim 17, further comprising a display displaying the icon indicating a temperature of the ultrasound system.

19. The ultrasound system as recited in claim 17, wherein the portable battery powered ultrasound imaging system weighs less than fifteen pounds.

20. The ultrasound system as recited in claim 17, wherein the temperature sensing device comprises a plurality of temperature sensors sensing temperatures of a plurality of portions of the ultrasound system, and the thermal management system controls temperature of the ultrasound system based on the plurality of sensed temperatures.

21. The ultrasound system as recited in claim 17, wherein the ultrasound system further comprises circuitry forming an ultrasound image, and the thermal management system controls temperature by controlling power dissipation in the circuitry.

22. The ultrasound system as recited in claim 21, wherein the thermal management system controls power dissipation by controlling clocking of the circuitry.

23. The ultrasound system as recited in claim 21, wherein the thermal management system controls power dissipation by controlling a mode in which the circuitry is operated.

24. The ultrasound system as recited in claim 17, wherein the ultrasound system further comprises a rechargeable battery and the thermal management system controls temperature by controlling charging of the rechargeable battery.

25. The ultrasound system as recited in claim 17, further comprising a fan, a rechargeable battery and circuitry forming an ultrasound image, wherein the thermal management system further controls temperature by controlling at least one of the fan, rechargeable battery and circuitry forming the ultrasound image.

26. The ultrasound system as recited in claim 17, further comprising a fan, a rechargeable battery and circuitry forming an ultrasound image, and wherein the temperature sensing device includes a plurality of temperature sensors sensing respective temperatures of an area near the fan, the rechargeable battery and the circuitry forming the ultrasound image, and wherein the thermal management system further controls temperature based on the plurality of sensed temperatures.

27. A method of controlling temperature of an electronic device, comprising:

reading a plurality of temperatures sensed by a plurality of temperature sensors;

determining a temperature of the electronic device based on the plurality of temperatures;

comparing the temperature of the electronic device with a plurality of predetermined temperature levels;

determining a type of temperature control action performed to control temperature of the electronic device from among a plurality of temperature control actions based on the result of the comparison; and controlling temperature of the electronic device in accordance with the determined temperature control action, wherein controlling temperature of the electronic device includes maintaining the temperature of the electronic device below a predetermined temperature, further comprising displaying an icon configured to display an indication that a temperature is approaching an overheated state, further performing a temperature management control hierarchy of control that first disables clocks, then controls a cooling fan, and finally displays an indication that a temperature of the electronic device exceeds a predetermined temperature.

28. A computer readable storage medium encoded with processing instructions for implementing a method of controlling temperature of an electronic device, the method comprising:

reading a plurality of temperatures sensed by a plurality of temperature sensors;

determining a temperature of the electronic device based on the plurality of temperatures;

comparing the temperature of the electronic device with a plurality of predetermined temperature levels;

determining a type of temperature control action performed to control temperature of the electronic device from among a plurality of temperature control actions based on the result of the comparison; and controlling temperature of the electronic device in accordance with the determined temperature control action, wherein controlling temperature of the electronic device includes maintaining the temperature of the electronic device below a predetermined temperature, further comprising displaying an icon configured to display an indication that a temperature is approaching an overheated state, further performing a temperature management control hierarchy of control that first disables clocks, then controls a cooling fan, and finally displays an indication that a temperature of the electronic device exceeds a predetermined temperature.

* * * * *